US006694179B1

United States Patent
Mouchawar et al.

(10) Patent No.: US 6,694,179 B1
(45) Date of Patent: Feb. 17, 2004

(54) DISPLAY FOR AND METHOD OF DISPLAYING ELECTROGRAMS RECEIVED FROM AN IMPLANTABLE CARDIAC STIMULATION DEVICE

(75) Inventors: Gabriel A. Mouchawar, Newhall, CA (US); James D. Causey, III, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 217 days.

(21) Appl. No.: 09/967,292

(22) Filed: Sep. 27, 2001

(51) Int. Cl.[7] .............................................. A61B 5/044
(52) U.S. Cl. ...................................... 600/523; 600/525
(58) Field of Search .................................. 600/523, 525

(56) References Cited

U.S. PATENT DOCUMENTS

| | | | |
|---|---|---|---|
| 4,072,851 A | 2/1978 | Rose ........................... | 364/487 |
| 4,625,278 A | * 11/1986 | Wong .......................... | 364/417 |
| 4,964,410 A | 10/1990 | Leahey et al. ............... | 128/696 |
| 4,989,610 A | * 2/1991 | Patton et al. ................ | 128/695 |
| 6,161,039 A | * 12/2000 | Krichen et al. .............. | 600/523 |
| 6,266,555 B1 | * 7/2001 | Werner et al. ............... | 600/523 |

OTHER PUBLICATIONS

Werner et al, "Single Complex Electrogram Display Having A Sensing Threshold for an Implantable Medical Device", US 2001/0031927–A1, Oct. 18, 2001.*

* cited by examiner

Primary Examiner—Carl Layno

(57) ABSTRACT

A display displays electrical activity of a heart. A receiver receives an electrical signal representing the electrical activity of a heart. The electrical signal includes event markers identifying occurrences of at least one type of cardiac event represented in the electrical signal. A display control circuit coupled to the display and to the receiver locates the display of the at least one type of cardiac event at a predetermined position on the display in response to the detection of one of the event markers. In at least one embodiment, the display overwrites the electrical signal. In another embodiment, a plurality of electrical signals may be stored and displayed simultaneously. In another embodiment, the stored plurality of electrical signals can be replayed to observe trends and patterns as the morphology changes.

33 Claims, 4 Drawing Sheets

DISPLAY FOR AND METHOD OF DISPLAYING ELECTROGRAMS RECEIVED FROM AN IMPLANTABLE CARDIAC STIMULATION DEVICE

FIELD OF THE INVENTION

The present invention generally relates to a display for and method of displaying electrograms received from an implantable cardiac device. The present invention more particularly relates to such a display and method which locates selected cardiac events at a predetermined location on a display screen to facilitate easier discernment of selected cardiac events and intervals.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as having two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Implantable cardiac stimulation devices conventionally include an internal telemetry circuit permitting the devices to communicate with an external programmer. The external programmers also include a telemetry circuit with an external antenna or "wand" which is held over the implant site to allow the communication between the programmer and the implanted device. With the communication channel thus established, the programmer permits the attending medical personnel to set device operating modes and stimulation and sensing parameters within the device. The communication channel also permits the device to convey to the external programmer operating and sensed physiological data for display. The physiological data may include an intracardiac electrogram (IEGM) or a plurality of IEGMs sensed across different portions of the heart. The IEGMs may be prestored in the device and conveyed to the programmer responsive to a suitable external command from the programmer. Along with the IEGMs, event markers may also be transmitted. The event markers represent sensing of cardiac events or the delivery of stimulation pulses. The event markers may represent sensing of intrinsic events such as P markers for P waves or R markers for R waves and delivery of stimulation pulses such as A markers for atrial stimulation pulses and V markers for ventricular stimulation pulses. When displayed, the event markers are aligned with their respective or corresponding event. The result is that physicians are provided with electrogram displays that provide more insight into the operation of the devices, the interaction of the device with the patient, and the underlying rhythm.

External displays, such as may be found in programmers for pacemakers and defibrillators display in real time or stored electrograms. Typically, the display scrolls while the electrograms, markers and interval information are being displayed on the display screen. While the electrograms scroll across the screen, event markers and associated interval information can occur anywhere on the screen. Since the electrogram display is being updated continuously, there is little time for the user to internalize the relative timing between events. As a result, most users must resort to making a printout of the displayed information to enable an analysis of the timing sequences in the electrograms.

SUMMARY OF THE INVENTION

The present invention provides a different approach to display electrograms. Instead of scrolling the display, the display is triggered by a cardiac event. The trigger may be either an intrinsic sensed event or an extrinsic paced event. As a result, the triggering event occurs in the same place on the display screen, locking the events and timing intervals to be discerned to that point.

In a single chamber device, there is usually a single IEGM channel to display. Therefore, the trigger may be a sensed P wave or R wave marker or a ventricular pacing pulse or atrial pacing pulse marker.

For a dual chamber device, where more than one IEGM channel is displayed, the user may select which IEGM channel to use as the triggering channel. For either a single chamber device or a dual chamber device, the user may also select the triggering event. For example, if the user is interested in measuring an AV delay, then either an A marker or P marker may be used as the triggering event. If, however, the user is more interested in discerning VA intervals, then either a V marker or R marker may be used as the triggering event.

The trigger point may be located at any desirable position on the horizontal axis of the display screen. Three positions which may provide the most benefit may be the one-eighth, middle or seven-eighths horizontal positions on the display screen since they allow observing both post-trigger and pre-trigger IEGM information.

In a special mode, the current waveform could be overlayed on top of a previous one or more waveforms, all having a common trigger event. The one or more previous waveforms could be distinguished by using different display characteristic (e.g., trace color, or other line attributes).

In the event that the IEGM telemetry has been received without event markers during a continuous time-out period, the display may then revert back to a scrolling display of the IEGM information. A warning message may also be presented to advise, for example, that pacing has been turned off or that severe under-sensing is occurring.

In accordance with the broader aspects of the present invention, the display includes a receiver that receives an electrical signal representing the electrical activity of a heart wherein the electrical signal includes event markers identifying occurrences of at least one type of cardiac event represented in the electrical signal. A display control circuit coupled to a display and to the receiver locates the display of the at least one type of cardiac event at a predetermined position on the display in response to the event markers.

As a result, the event marker within the electrical signal is detected. Responsive to such detection, the electrogram is displayed on the display with a selected cardiac event within the electrogram being at a predetermined location on the display.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
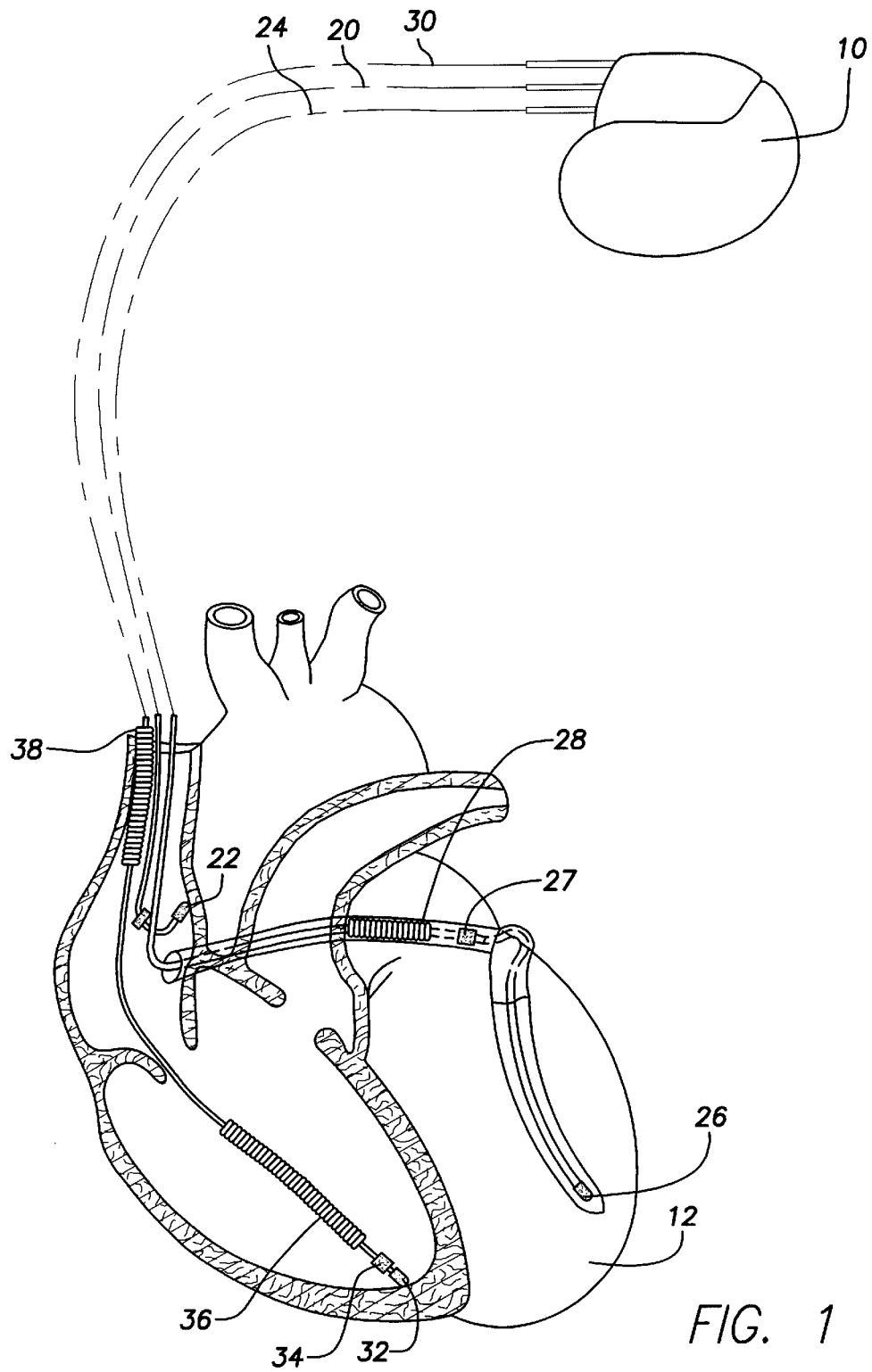
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
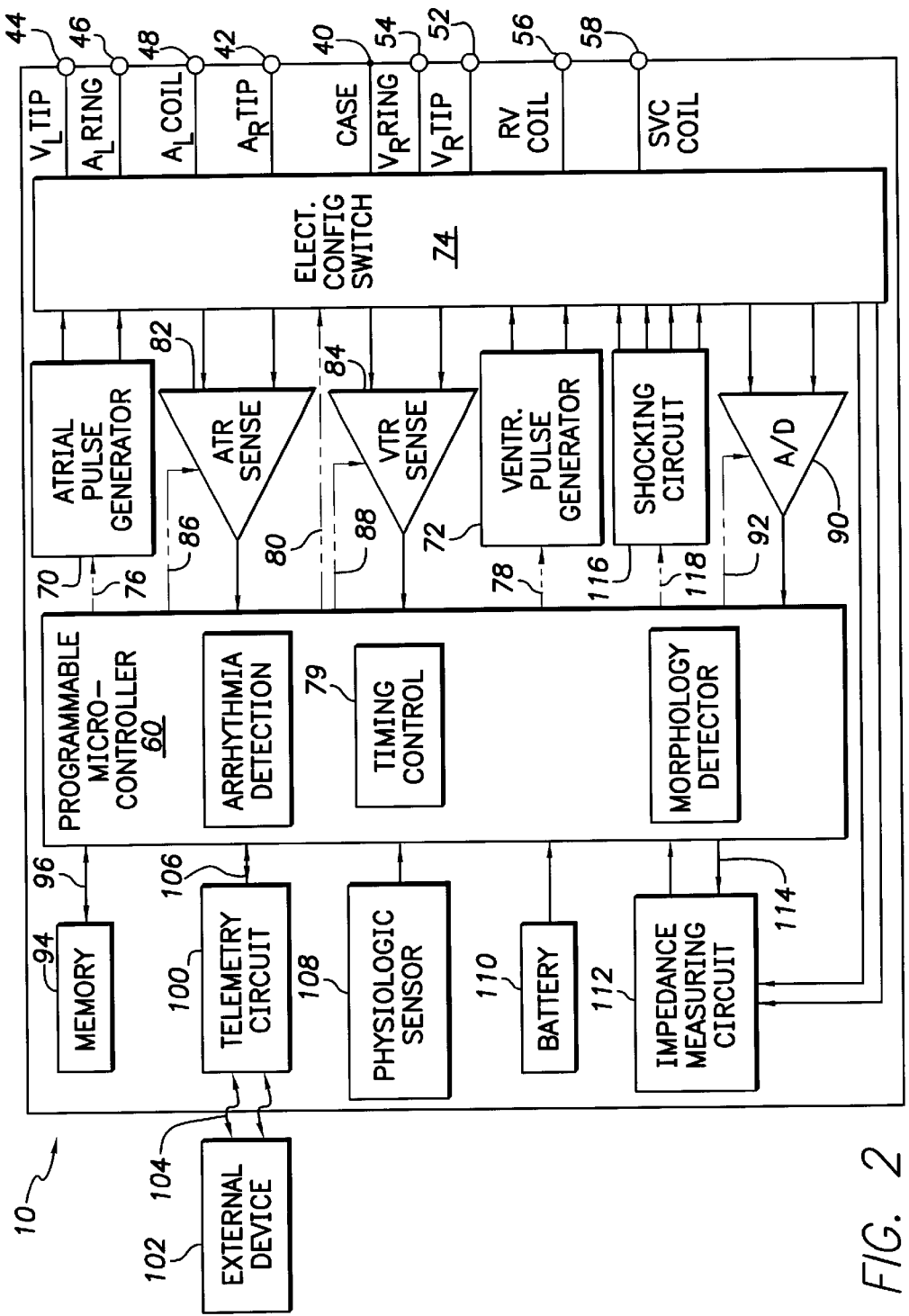
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. Along with the one or more channels of electrogram data, the telemetry circuit 100 also may transmit event markers identifying corresponding cardiac events in the electrograms. The event markers may identify intrinsic events such as R markers for sensed R waves and P markers for sensed P waves or they may identify extrinsic events such as V markers for ventricular stimulation pulses or A markers for atrial stimulation pulses. When more than one IEGM channel is transmitted, such as those provided by a dual chamber pacemaker, the IEGM channel data is preferably segregated into respective frames which are demultiplexed when received by the external device 102. The event markers transmitted with the IEGM data may each contain a different code to enable identification of the transmitted event markers. In this manner, the various R markers, V markers, P markers, and A markers may be selected or identified for detection. Such detection will be described subsequently.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive electrogram data through the telemetry circuits 100.

As further shown in FIG. 2, the device 10 is shown as having an impedance measuring circuit 112 which is enabled by the microcontroller 60 via a control signal 114. The impedance measuring circuit 112 is not critical to the present invention and may be of the type well known in the art. Hence, it is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
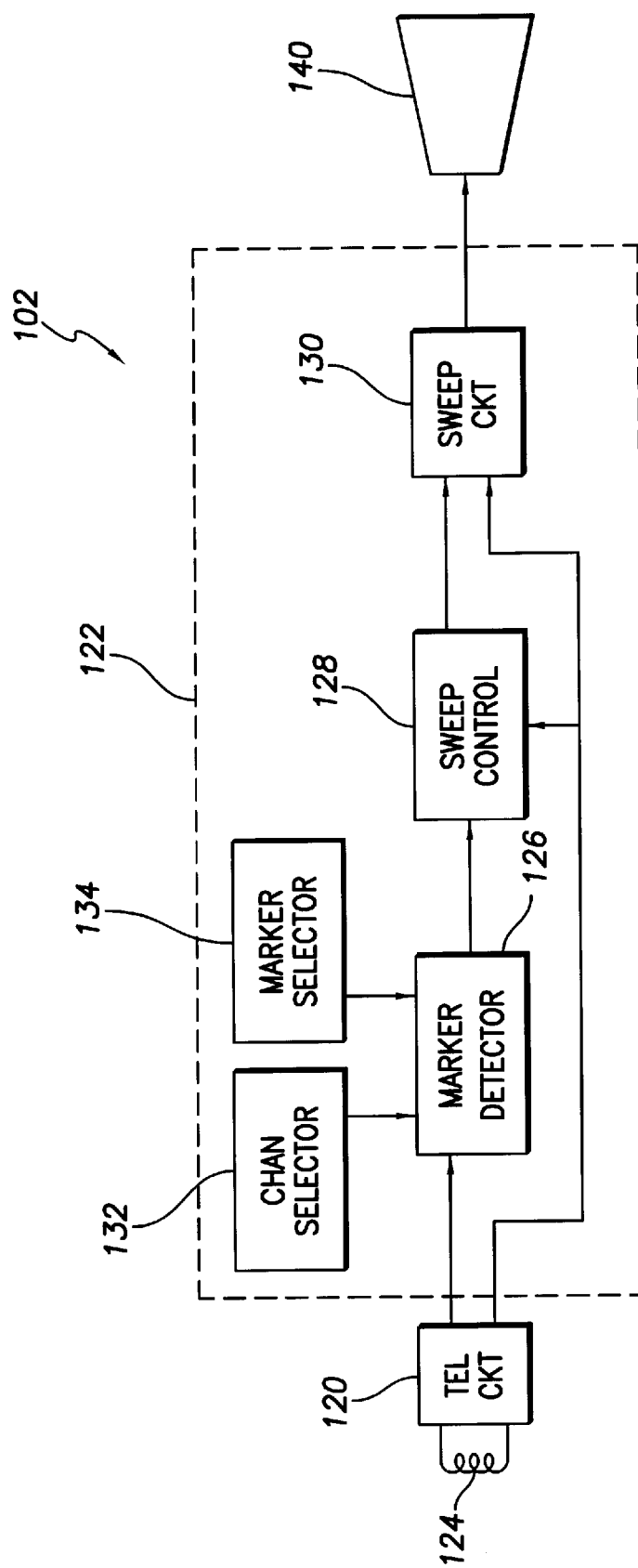
FIG. 3 is a block diagram of a display embodying the present invention.

Referring now to FIG. 3, it shows a block diagram of the elements which may be employed within the external device 102 for displaying one or more electrograms in accordance with a preferred embodiment of the present invention. The external or display device 102 includes a telemetry circuit 120, a display control circuit 122, and a display 140.

The telemetry circuit 120 may be of the type well known in the art for receiving the telemetered electrogram data transmitted by the telemetry circuit 100 of the device 10 over the communication link 104. To that end, the telemetry circuit includes an antenna 124 for receiving the telemetered electrical signal containing the one or more electrograms. The telemetry circuit 120 forms a receiver or input means for receiving the transmitted electrical signal containing the heart activity signal(s) or electrogram data representing electrical activity of the patient's heart across one or more portions of the patient's heart. As previously mentioned, included within the transmitted signal along with the electrogram or electrograms to be displayed are the event markers for each electrogram channel. Each type of event marker (R marker, V marker, P marker, A marker) has its own respective digital code to permit selective detection of the event markers.

The display control circuit 122 is coupled to the display 140 and to the telemetry circuit 120. If a single electrogram channel is received, the display control circuit 122 locates the display of the electrogram on the display 140 with the cardiac event of the electrogram represented by a corresponding selected event marker at a predetermined location on the display 140 responsive to detection of the event marker. If more than one electrogram channel is received, the display control circuit locates a selected electrogram on the display 140 with the selected cardiac event at a predetermined location on the display 140 responsive to detection of its corresponding event marker. The remaining electrogram or electrograms which are not selected may then be displayed with the selected electrogram arranged in a predetermined time relation to the selected electrogram. Preferably, the electrograms are vertically arrayed on the display and aligned in a time coherent manner.

The display control circuit 122 includes an event marker detector 126, a sweep control circuit 128 and a sweep circuit 130. The marker detector 126 is coupled to the telemetry circuit 120 for receiving the received electrical signal including the electrogram data channels and the event markers for each channel. The display control circuit 122 also includes a channel selector 132 and an event marker selector 134. The event marker selector 134 causes the event marker detector 126 to detect for a selected type of event marker while the channel selector 132 controls in which electrogram channel the marker detector 126 is to detect for the selected event marker from which the display is to be triggered.

When the selected event marker is detected by the marker detector 126, it generates a time stamp which is conveyed to the sweep control circuit 128. The sweep control circuit 128 is also coupled to the telemetry circuit 120 for receiving the received electrogram data. Upon receiving the time stamp of the detected event marker from the marker detector 122, the sweep control circuit 128 uses the time stamp to locate the cardiac event corresponding to the detected time stamp. It then triggers the sweep circuit 130 to display the selected cardiac event of the selected electrogram channel at the predetermined location on the display 140.

Figure 4:
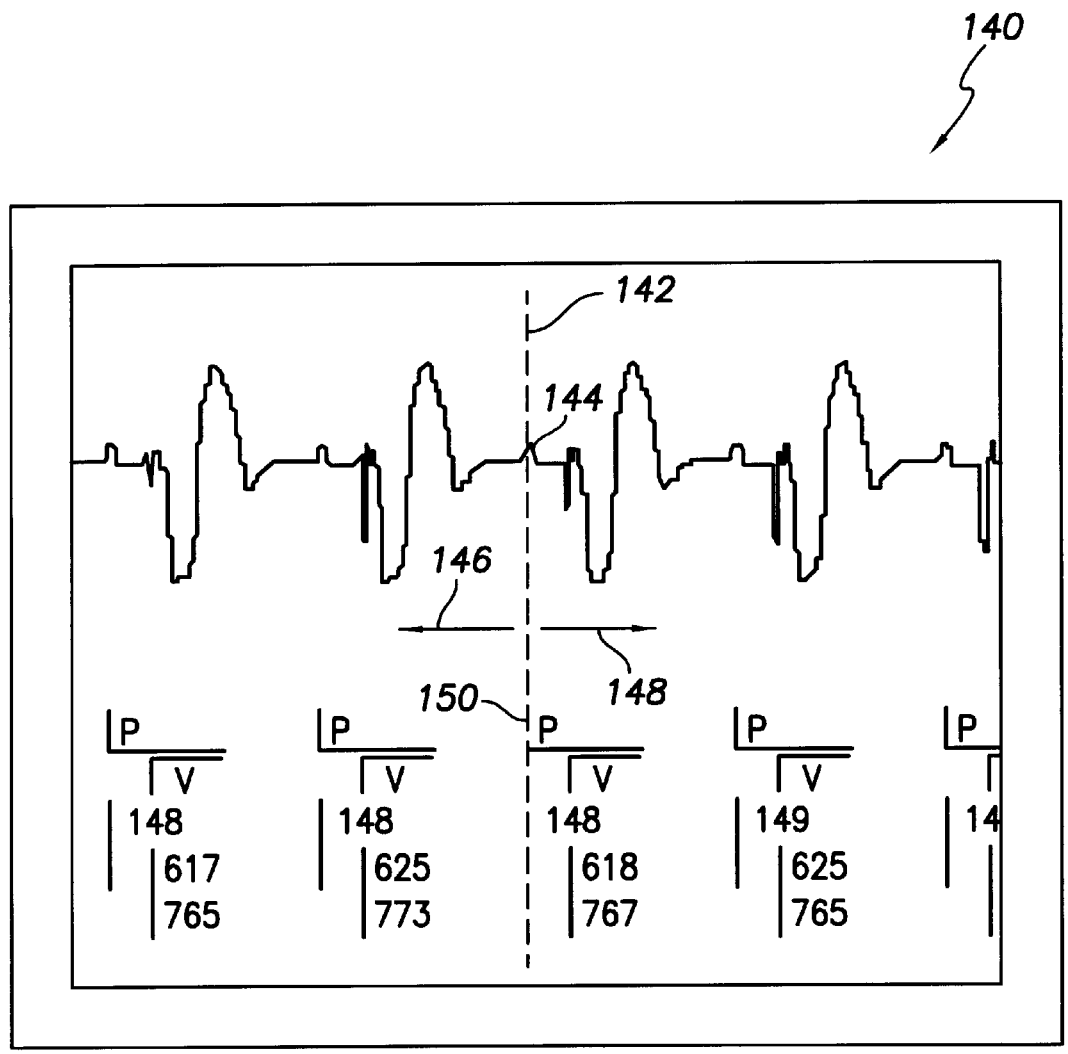
FIG. 4 is an electrogram display illustrating particular features afforded by the present invention.

FIG. 4 shows what the appearance of the display may be for displaying a single electrogram with a selected cardiac event in the center of the display horizontal axis. The center of the display 140 is shown by the center line 142. Here the selected event marker from which to trigger is the P marker 150 identifying a sensed P wave 144. After triggering the sweep circuit to display the P wave 144 and its corresponding P marker 150 in the center of the screen, the sweep control circuit 130 preferably sweeps toward the left as indicated by arrow 146 to fill in the pre-trigger IEGM and then returns to the centerline 142 and sweeps to the right as indicated by arrow 148 to fill in the post-trigger IEGM. The foregoing is repeated upon the next display update.

In one embodiment, in a special mode, instead of the current electrogram replacing the previous electrogram, the current electrogram could be overlayed on top of a previous one or more electrograms; all such waveforms having a common trigger event. The one or more previous electrograms could be distinguished by using different display characteristic (e.g., trace color, or other line attributes).

In yet another embodiment, the microcontroller 60, or the external device 102, could trigger the storage of "n" of the most recent electrogram displays and allow playback of the stored waveforms so as to reveal changes or trends in the complexes (e.g., trends in the S-T segments or spurious conduction changes, etc.).

As will be noted from FIG. 4, since a P wave will always appear in the center of the display 140, an interval such as the PV interval may be readily discerned. This is made possible because the display is not continuously scrolling. Of course, any one of the other available event markers may be used as the display trigger. Also, even though just one electrogram is illustrated in FIG. 4, those skilled in the art would appreciate that other, nonselected electrograms may also be displayed and vertically arrayed in a predetermined time relation, such as by time coherence, to the selected electrogram.

If the selected event marker is not detected during a continuous time-out period, the display control circuit 122 may revert to scrolling operation. This may be accompanied with a visual warning of under sensing or lack of pacing pulses.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An apparatus for displaying electrical activity of a heart, comprising:

a receiver that receives an electrical signal representing the electrical activity of a heart, the electrical signal comprising event markers identifying occurrences of at least one type of cardiac event represented in the electrical signal;

a display, coupled to the receiver, that displays a visual image of the electrical signal; and a display control circuit, coupled to the display and to the receiver, that is responsive to the event markers to position the display of the at least one type of cardiac event at a predetermined position on the display:

wherein the display control circuit further positions a pre-trigger cardiac information prior to the at least one type of cardiac event on the display and further positions a post-trigger cardiac information subsequent to the at least one type of cardiac event on the display.

2. The apparatus of claim 1, wherein the display control circuit includes an event marker detector, coupled to the receiver, that detects the event markers.

3. The apparatus of claim 1, wherein the display control circuit locates the display of the at least one type of cardiac event at a predetermined horizontal position on the display.

4. The apparatus of claim 1, wherein:

the event markers include a plurality of different types of event markers corresponding to respective ones of a like number of different types of cardiac event; and the display control circuit includes a selector that selects the event markers corresponding to the at least one type of cardiac event from among the plurality of different types of event markers.

5. The apparatus of claim 4, wherein the display control circuit includes:

an event marker detector, coupled to the selector and to the receiver, that detects the event markers corresponding to the at least one type of cardiac event.

6. The apparatus of claim 4, wherein the plurality of different types of event markers includes event markers corresponding to intrinsic cardiac events.

7. The apparatus of claim 1, wherein the pre-trigger cardiac information is a pre-trigger electrogram and the post-trigger cardiac information is a post-trigger electrogram.

8. An apparatus for displaying electrical activity of a heart, comprising:

a receiver that receives an electrical signal representing the electrical activity of a heart, the electrical signal comprising event markers identifying occurrences of at least one type of cardiac event represented in the electrical signal;

a display, coupled to the receiver, that displays a visual image of the electrical signal; and a display control circuit, coupled to the display and to the receiver, that is responsive to the event markers to position the display of the at least one type of cardiac event at a predetermined position on the display;

wherein the event markers include a plurality of different types of event markers corresponding to respective ones of a like number of different types of cardiac event;

wherein the display control circuit includes a selector that selects the event markers corresponding to the at least one type of cardiac event from among the plurality of different types of event markers; and wherein the plurality of different types of event markers includes event markers corresponding to extrinsic cardiac events.

9. An apparatus for displaying electrical activity of a heart, comprising:

a receiver that receives an electrical signal representing the electrical activity of a heart, the electrical signal comprising event markers identifying occurrences of at least one type of cardiac event represented in the electrical signal;

a display, coupled to the receiver, that displays a visual image of the electrical signal; and a display control circuit, coupled to the display and to the receiver, that is responsive to the event markers to position the display of the at least one type of cardiac event at a predetermined position on the display;

wherein the receiver is configured to receive a plurality of electrical signal channels, the channels representing electrical activity across different portions of the heart and at least one channel including event markers identifying the at least one type of cardiac event; and wherein the display control circuit includes a channel selector and an event marker selector for locating the at least one type of cardiac events corresponding to a selected event marker of a selected channel at a predetermined position on the display and aligning non-selected channels in a predetermined time relation to the selected channel on the display in response to the selected event marker.

10. The apparatus of claim 1, wherein the display control circuit refreshes the display with a current electrical signal with each triggered event marker, thereby replacing a most recent electrical signal with the current electrical signal.

11. The apparatus of claim 1, wherein the display control circuit displays one or more previous electrical signals, each electrical signal being triggered by a common event marker, thereby overlaying one or more of the previous electrical signals with the current electrical signal.

12. An apparatus for displaying electrical activity of a heart, comprising:

a receiver that receives an electrical signal representing the electrical activity of a heart, the electrical signal comprising event markers identifying occurrences of at least one type of cardiac event represented in the electrical signal;

a display, coupled to the receiver, that displays a visual image of the electrical signal; and a display control circuit, coupled to the display and to the receiver, that is responsive to the event markers to position the display of the at least one type of cardiac event at a predetermined position on the display;

wherein the display control circuit displays one or more previous electrical signals, each electrical signal being triggered by a common event marker, thereby overlaying one or more of the previous electrical signals with the current electrical signal; and wherein the display control circuit displays the one or more previous electrical signals using different display characteristics for each respective electrical signal.

13. An apparatus for displaying electrical activity of a heart, comprising:

a receiver that receives an electrical signal representing the electrical activity of a heart, the electrical signal comprising event markers identifying occurrences of at least one type of cardiac event represented in the electrical signal;

a display, coupled to the receiver, that displays a visual image of the electrical signal;

a display control circuit, coupled to the display and to the receiver, that is responsive to the event markers to position the display of the at least one type of cardiac event at a predetermined position on the display;

wherein the display control circuit displays one or more previous electrical signals, each electrical signal being triggered by a common event marker, thereby overlaying one or more of the previous electrical signals with the current electrical signal; and a storage device that stores a predetermined number of the previous electrical signals; and wherein the display control circuit includes circuitry for replaying of the stored electrical signals.

14. A display for displaying an electrical signal including an electrogram representing electrical activity of a heart and an event marker identifying an occurrence of a selected cardiac event represented in the electrogram, the display comprising:

input means for receiving the electrical signal;

display means for providing a visual image display of the electrogram;

detecting means for detecting the event marker in the electrical signal; and display control means, responsive to the detecting means and coupled to the display means, for positioning the selected cardiac event of the electrogram at a predetermined location on the display means in response to the detection of the event marker by the detecting means;

wherein the display control means further positions a pre-trigger electrogram prior to the selected cardiac event on the display means and further positions a post-trigger electrogram subsequent to the selected cardiac event on the display means.

15. The display of claim 14, wherein the display control means includes sweep control means for locating the selected cardiac event of the electrogram at a predetermined horizontal position on the display means.

16. The display of claim 14, wherein:

the electrical signal includes a plurality of different types of event markers, each type of event marker corresponding to different respective types of cardiac events in the electrogram; and the display includes selecting means coupled to the detecting means for selecting the event marker corresponding to the selected cardiac event from among the plurality of different types of event markers.

17. The display of claim 16, wherein the plurality of different types of event markers include event markers corresponding to intrinsic cardiac events.

18. The display of claim 13, wherein the input means comprises telemetry means for receiving a transmitted electrical signal containing the electrogram to be displayed.

19. The display of claim 14, wherein the display control means includes means for replacing a most recent electrical signal with a current electrical signal.

20. The display of claim 14, the display control means includes means for overlaying one or more of the previous electrical signals together with the current electrical signal.

21. A display for displaying an electrical signal including an electrogram representing electrical activity of a heart and an event marker identifying an occurrence of a selected cardiac event represented in the electrogram, the display comprising:

input means for receiving the electrical signal;

display means for providing a visual image display of the electrogram;

detecting means for detecting the event marker in the electrical signal; and display control means, responsive to the detecting means and coupled to the display means, for positioning the selected cardiac event of the electrogram at a predetermined location on the display means in response to the detection of the event marker by the detecting means;

wherein the electrical signal includes a plurality of different types of event markers, each type of event marker corresponding to different respective types of cardiac events in the electrogram;

wherein the display includes selecting means coupled to the detecting means for selecting the event marker corresponding to the selected cardiac event from among the plurality of different types of event markers; and wherein the plurality of different types of event markers include event markers corresponding to extrinsic cardiac events.

22. A display for displaying an electrical signal including an electrogram representing electrical activity of a heart and an event marker identifying an occurrence of a selected cardiac event represented in the electrogram, the display comprising:

input means for receiving the electrical signal;

display means for providing a visual image display of the electrogram;

detecting means for detecting the event marker in the electrical signal; and display control means, responsive to the detecting means and coupled to the display means, for positioning the selected cardiac event of the electrogram at a predetermined location on the display means in response to the detection of the event marker by the detecting means;

wherein the input means comprises telemetry means for receiving a transmitted electrical signal containing the electrogram to be displayed;

wherein the telemetry means is configured to receive a plurality of electrical signal channels, each channel including an electrogram representing electrical activity between respective portions of the heart and at least one channel including event markers identifying the selected cardiac event; and wherein the display means includes selecting means for selecting one of the channels and a selected event marker within the selected channel, the display control means locating the selected cardiac event, corresponding to the selected event marker within the selected channel at a predetermined position on the display means and including means for aligning non-selected channels in a predetermined time relation to the selected channel on the display in response to the selected event marker.

23. A display for displaying an electrical signal including an electrogram representing electrical activity of a heart and an event marker identifying an occurrence of a selected cardiac event represented in the electrogram, the display comprising:

input means for receiving the electrical signal;

display means for providing a visual image display of the electrogram;

detecting means for detecting the event marker in the electrical signal; and display control means, responsive to the detecting means and coupled to the display means, for positioning the selected cardiac event of the electrogram at a predetermined location on the display means in response to the detection of the event marker by the detecting means;

wherein the display control means includes means for overlaying one or more of the previous electrical signals together with the current electrical signal; and wherein the display control means includes means for using different display characteristics for each respective electrical signal to enhance visually distinguishing each signal.

24. A method of displaying on a display an electrogram contained in an electrical signal also including an event marker representing a given type of cardiac event within the electrogram, the method comprising:

detecting the event marker within the electrical signal;

responsive to detecting the event marker, displaying the electrogram at a predetermined location on the display based on the given type of cardiac event within the electrogram; and displaying on the display a pre-trigger electrogram to prior to the electrogram and displaying on the display a post-trigger electrogram subsequent to the electrogram.

25. The method of claim 24, wherein the step of displaying the electrogram includes locating the given type of cardiac event within the electrogram at a predetermined horizontal location on the display.

26. The method of claim 24, wherein the electrical signal includes a plurality of different types of event markers each corresponding to a different type of cardiac event, and wherein the detecting step includes the step of selecting the given type of event marker from among the plurality of different types of event markers.

27. The method of claim 24, including the further steps of:

transmitting the electrical signal from an implantable cardiac device; and receiving the electrical signal prior to detecting the event marker within the electrical signal.

28. The method of claim 27, wherein:

the transmitting step includes transmitting a plurality of electrical signal channels, each channel including an electrogram and at least one channel including the event marker; and the displaying step includes displaying all of the electrograms of the channels on the display with the given type of cardiac event within the electrogram of the at least one channel at a predetermined location on the display and aligning the electrograms of the channels other than the at least one channel in predetermined time relation to the electrogram of the at least one channel on the display.

29. A method of displaying on a display an electrogram contained in an electrical signal also including an event marker representing a given type of cardiac event within the electrogram, the method comprising:

detecting the event marker within the electrical signal; and responsive to detecting the event marker, displaying the electrogram at a predetermined location on the display based on the given type of cardiac event within the electrogram;

wherein the displaying step includes clearing the display before displaying a subsequent electrical signal.

30. A method of displaying on a display an electrogram contained in an electrical signal also including an event marker representing a given type of cardiac event within the electrogram, the method comprising:

detecting the event marker within the electrical signal; and responsive to detecting the event marker, displaying the electrogram at a predetermined location on the display based on the given type of cardiac event within the electrogram;

wherein the displaying step includes displaying a plurality of previous electrical signals together with a current electrical signal, each electrical signal being triggered by a common event marker.

31. The method of claim 30, wherein the displaying step includes displaying each of the plurality of previous electrical signals using a respective display characteristic.

32. The method of claim 30, further comprising:

storing a plurality of electrical signals in chronological order; and replaying of the electrical signals in the stored chronological order.

33. A display for displaying an electrical signal including an electrogram representing electrical activity of a heart and an event marker identifying an occurrence of a selected cardiac event represented in the electrogram, the display comprising:

input means for receiving the electrical signal;

display means for providing a visual image display of the electrogram;

detecting means for detecting the event marker in the electrical signal; and display control means, responsive to the detecting means and coupled to the display means, for positioning the selected cardiac event of the electrogram at a predetermined location on the display means in response to the detection of the event marker by the detecting means wherein the display control means includes means for overlaying one or more of the previous electrical signals together with the current electrical signal;

means for storing a predetermined number of previous electrical signals; and wherein the display control means includes means for repetitively displaying the stored electrical signals.

* * * * *